United States Patent [19]

Harner et al.

[11] Patent Number: 4,988,155
[45] Date of Patent: Jan. 29, 1991

[54] IN-LINE FIBER OPTIC PROBE INTERFACE

[75] Inventors: Richard S. Harner; Charles J. Myers, both of Midland, Mich.

[73] Assignee: The Dow Chemical Company, Midland, Mich.

[21] Appl. No.: 369,745

[22] Filed: Jun. 22, 1989

[51] Int. Cl.$^5$ .............................................. G02B 6/00
[52] U.S. Cl. .............................. 350/96.1; 250/227.11; 356/440; 356/246
[58] Field of Search ................ 250/227; 356/246, 440; 350/96.1, 96.15, 96.2

[56] References Cited

U.S. PATENT DOCUMENTS

| 4,573,761 | 3/1986 | McLachlan et al. | 356/342 |
| 4,707,134 | 11/1987 | McLachlan et al. | 350/96.24 |
| 4,715,710 | 12/1987 | Andersen | 356/246 |
| 4,786,171 | 11/1988 | LeFebre et al. | 356/440 |

OTHER PUBLICATIONS

U.S. Pat. Appln. Ser. No. 07/236,571, "Sealed Fiber Optic Probe", filed Aug. 25, 1988, by Harner, et al.

*Primary Examiner*—William L. Sikes
*Assistant Examiner*—John Ngo
*Attorney, Agent, or Firm*—David S. Stallard; Thomas J. Burger; Timothy S. Stevens

[57] ABSTRACT

An in-line fiber optic probe interface includes a sample cell with a bore therein defining an optical axis. A controller housing is centered by O-ring seals in the bore and a pathlength controller is mounted on the housing. A fiber optic probe is disposed in the housing and controller, sealed thereto by o-ring seals at multiple points to maintain the probe in appropriate alignment on the optical axis.

26 Claims, 3 Drawing Sheets

PRIOR ART

FIG. 5

IN-LINE FIBER OPTIC PROBE INTERFACE

This invention relates to apparatus for optically sampling fluids, and more particularly to an in-line fiber optic probe interface wherein the accuracy and consistency of the optical alignment of each probe is maximized.

BACKGROUND OF THE INVENTION

In-line fiber optic probes have been used for identifying, or for monitoring the parameters of, a fluid flowing in a sample, recirculating or a process line. Examples of such probes are found in U.S. Pat. Nos. 4,573,761 and 4,707,134, incorporated herein by reference. An improved probe of this type is described in pending U.S. Pat. application Ser. No. 07/236,571, entitled "Sealed Fiber Optic Probe", filed Aug. 25, 1988, also incorporated herein by reference. These disclosures are not essential to an understanding or description of the invention of this application, but are included for background purposes.

In sampling fluid by spectrophotometry, one typical practice has been to mount two fiber optic probes such that their ends face each other across a gap. Fluid flows in this gap while light from one probe is directed through the fluid to the other probe. The light received is analyzed by known spectrophotometry processes to provide identification of the fluid or monitoring of selected parameters thereof.

Typically, the probes are mounted in a tubular body or cell which also has a fluid inlet, a fluid outlet and a fluid passageway extending the gap between the probe ends. One such device is an in-line absorbance cell manufactured by Guided Wave Inc., of El Dorado Hills, Calif. In that device, fiber optic probes are mounted by means of compression ferrule seal fittings mounted in the opposite ends of a tube. Such fittings include ferrule and compression members which interact to engage the probes. The ends of the probes are spaced apart and a fluid inlet and outlet are disposed in the tube sidewall for passing fluid through the tube and between the probe ends.

The consistency of optical alignment of each probe in such a device is poor, due mainly to the large tolerance ranges produced by the compression ferrule seal fittings, the relatively loose fit of probe to fitting and the use of diverse fitting materials. These fittings tend to establish a pivot point or axis about which the probe moves or wanders away from its desired alignment when the device is adjusted or subjected to pressure or temperature changes.

In such forms of probe mounting, fitting threads according to National Pipe Thread standards allow a sloppy fit for pipe and adapter matings to be sealed with pipe dope. Such designs allow significant tolerance build-up, producing inconsistent optical alignment of an associated probe. Also, depending on the fluids to be tested, a sampling system may require exotic fitting and seal materials which are very expensive and require long lead times to produce.

Moreover, the different coefficients of expansion and the rigidity of diverse materials used in the same system generate further optical misalignment when the system is pressured or temperatures change. Such pressure and temperature changes can cause different material responses and can flex such a system, causing significant optical misalignment.

It should be appreciated that proper optical alignment of probes is a critical consideration whether probes are mounted on a common co-axial axis, as in the aforementioned in-line absorbance cell, or are mounted on respective optical intersecting axes at some predetermined angular disposition, such as in certain fluorescent, scattering or other techniques. If the probes in any such optical systems are misaligned, system efficiency is reduced. Moreover, shifts in alignment due to temperature or pressure changes are seen falsely by the system as fluid or parameter fluctuations.

Accordingly, it has been one objective of the invention to provide an in-line fiber optic probe interface with improved optical alignment of each probe, whether coaxially or otherwise aligned.

SUMMARY OF THE INVENTION

To this end, a preferred embodiment of the invention includes an in-line fiber optic probe interface including a sample cell or pipe cross wherein two cooperating probes are mounted on a common optical axis. Means are provided for mounting each probe in predetermined optical alignment.

Flats are machined on the sample cell or pipe cross. Probe receiving bores are drilled in the cell with reference to these flats. All other machining operations are derived or oriented from this bore and its axis. Flanged controller housings, provided with internal and external 0-ring seals, are inserted into the bore from each side of the sample cell, with the flanges disposed on the machined surfaces. The controller housings are centered by the 0-ring seals and then mounting holes are then drilled and tapped through the controller housing flanges into the sample cell. The housing axes are thus centered and held with respect to the bore axes.

A probe is inserted into each side of the sample cell through a respective controller housing. The probes are sealed and centered therein by means of the internal O-rings in the controller housings.

A pathlength controller is disposed around each probe and is threaded into the respective controller housing. An O-ring seal is disposed between the pathlength controller and the rearward end of each probe such that the probe is sealed and centered at its rearward end as well.

A split retainer ring is disposed in a groove on each probe and is captured by a pathlength controller cap. When the pathlength controller is rotated, the probe is adjusted longitudinally along its axis to vary the path length between the respective probe ends. The probe itself is preferably not turned in this embodiment since the retainer ring may slip in the probe groove or controller cap or both.

The sample cell or pipe cross is provided with fluid inlet and outlet means and a passageway for flowing fluid therethrough and in the gap between the probe ends. The sample cell or pipe cross can either constitute a spacer between two flanged fluid pipe ends, when used in process monitoring, for example, or a fluid sampling or recirculation line can be connected thereto by appropriate fittings and valves when the interface is used for fluid identification, for example.

It will be appreciated that each probe is aligned on its optical axis by means of the self centering O-rings at multiple locations on the probe, at a forward end in the controller housing and more rearwardly in the pathlength controller. This construction accurately aligns each probe on its predetermined optical axis, while the multiple point O-ring support maintains the alignment despite temperature or pressure variations, or longitudinal probe adjustment.

Where desired, a further fluid inlet and outlet can be provided in the sample cell or pipe cross for cleaning or flushing fluid, or to provide access to the probe ends for inspection, calibration or other operations.

While this embodiment contemplates two probes accurately maintained on a common coaxial optical axis to form an in-line interface, it will be appreciated the invention contemplates means for accurately mounting and maintaining a single probe on a predetermined optical axis, whether or not coaxial with other probes.

Accordingly, the interface described herein produces an improved and more consistently maintained probe alignment, provides for pathlength modification, provides controlled optical alignment under process conditions of changing temperature and pressure and eliminates the need for exotic or expensive ferruletype fittings.

BRIEF DESCRIPTION OF THE DRAWINGS

These and other features and advantages of the invention will become apparent from the following detailed description of a preferred embodiment and from the drawings in which.

DETAILED DESCRIPTION OF THE DRAWINGS

Figure 5:
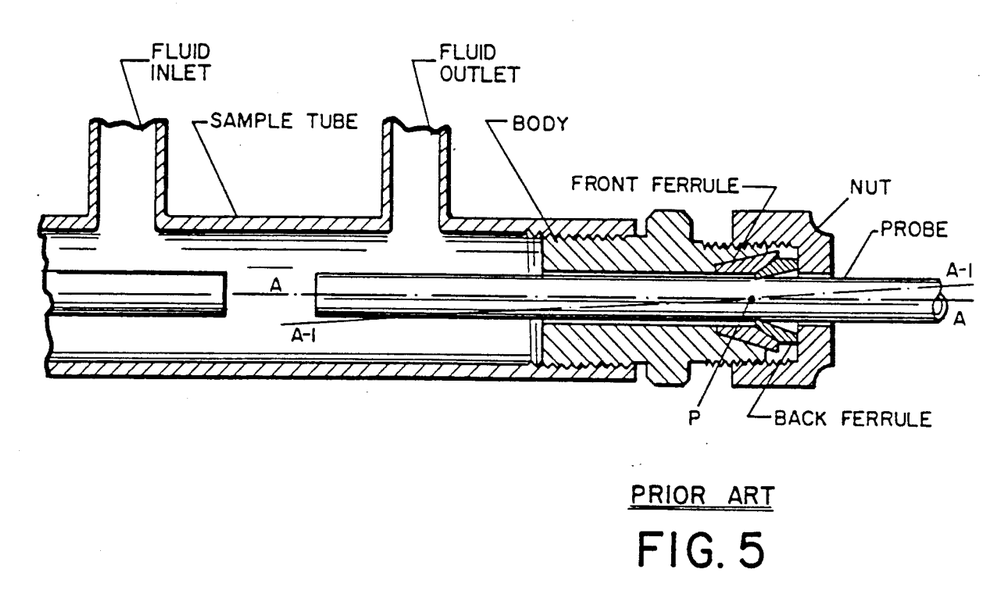
FIG. 5 is an enlarged cross-sectional view of a prior art in-line absorbance cell.

Turning now to the drawings and first to FIG. 5 thereof, there is shown a diagrammatic sketch of a prior type in-line absorbance cell and fitting used to mount a fiber optic probe therein. In this cell, a fiber optic probe is received within each end of a tube, the ends of the probes having a space therebetween. A fluid inlet and outlet are connected to the tube such that a fluid flows therethrough and in the space between the probe ends. Light from one probe passes through the fluid and is received by the other probe for analysis. Each probe is mounted in the tube by means of a compression fitting.

Such a system is used, for example, in the in-line absorbance cell of Guided Wave, Inc. of El Dorado Hills, Calif.

The prior art fitting is manufactured by the Swagelok Company of Solon, Ohio and is sold under the trademark, "Swagelok". A Swagelok fitting generally comprises four components including a body, a front ferrule, a back ferrule and a nut. In FIG. 5, the Swagelok body has been threaded into the sample tube. It, of course, could be welded or otherwise secured therein. Thereafter, a probe is disposed within the swagelok fitting and the nut is tightened to engage and compress the ferrules thereby engaging an holding the probe as shown.

It will be appreciated that this swagelok fitting primarily engages the probe in a circumferential area defining a point P in the area of the front and back ferrules. Due to the tolerances between the probe and the body of the Swagelok fitting, initial probe alignment on the axis A, as well as the continued retention of the probe in alignment with the axis A cannot be guaranteed. If the sample tube in the Swagelok fitting is subjected to pressures or temperatures, such changes can flex the entire system causing the probe to wander and become misaligned, for example, along the axis A-1 and about the point P. Such misalignment is highly undesirable since it can be seen by the sensing equipment attached to the probe as a change in the fluid parameters or fluid identity. The invention, with preferred and alternative embodiments as will be described in connection with FIGS. 1–4 herein, provides means by which optical alignment of each probe can be maintained.

It will be appreciated that the invention described herein can be utilized to produce and maintain proper and precise optical alignment of a fiber optic probe on a predetermined optical axis. The invention is readily adaptable for use with respective probes, although in the embodiments shown, the invention will be utilized in the disposition of two probes located on a common optical axis. Of course, utilization of the invention to mount probes on a predetermined optical axis, where the optical axes of the particular sample cell may intersect, rather than being coaxial, is contemplated.

Figure 1:
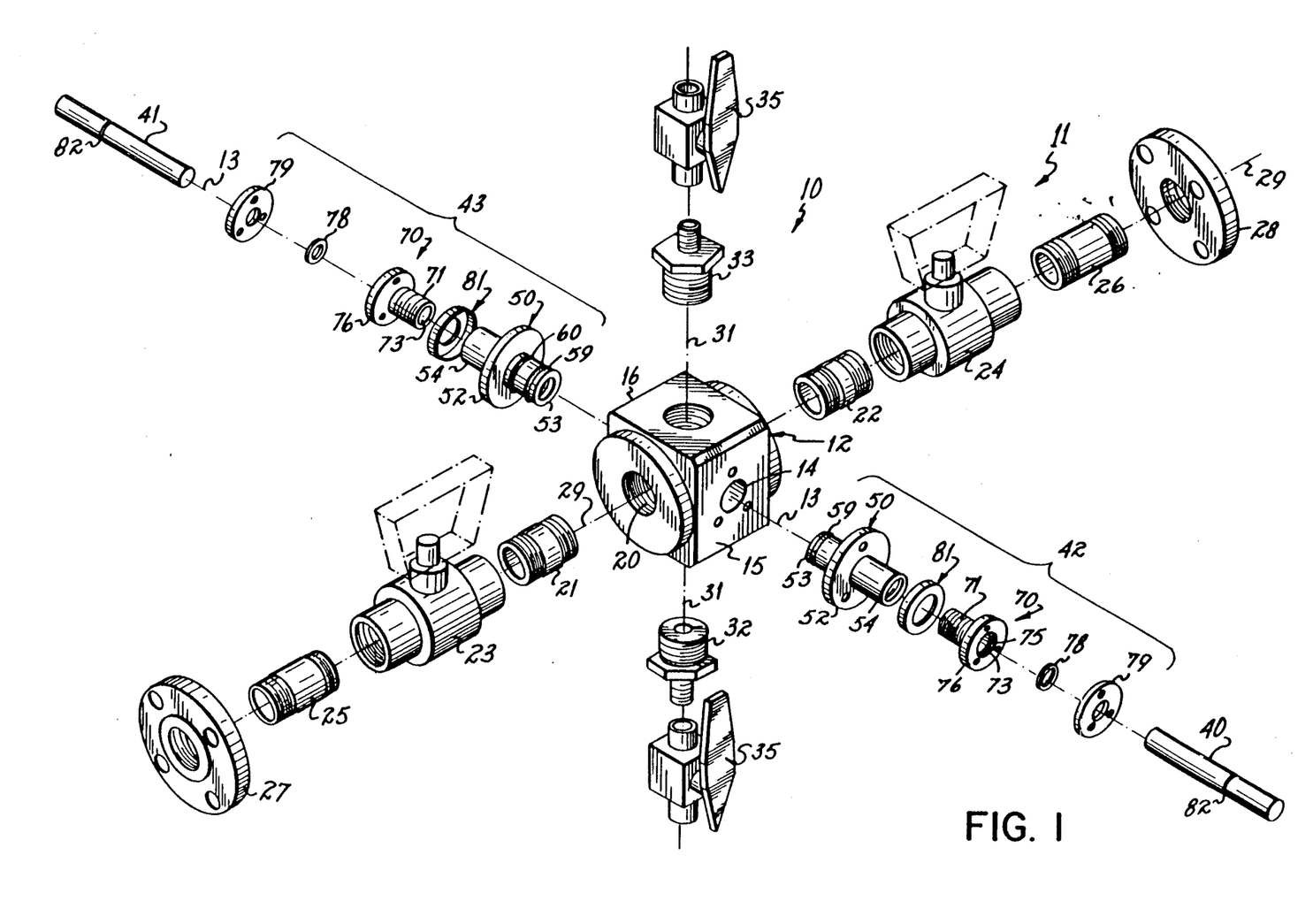
FIG. 1 is a perspective view of the interface of one embodiment of the invention in disassembled form showing the components thereof.
Figures 2, 4:
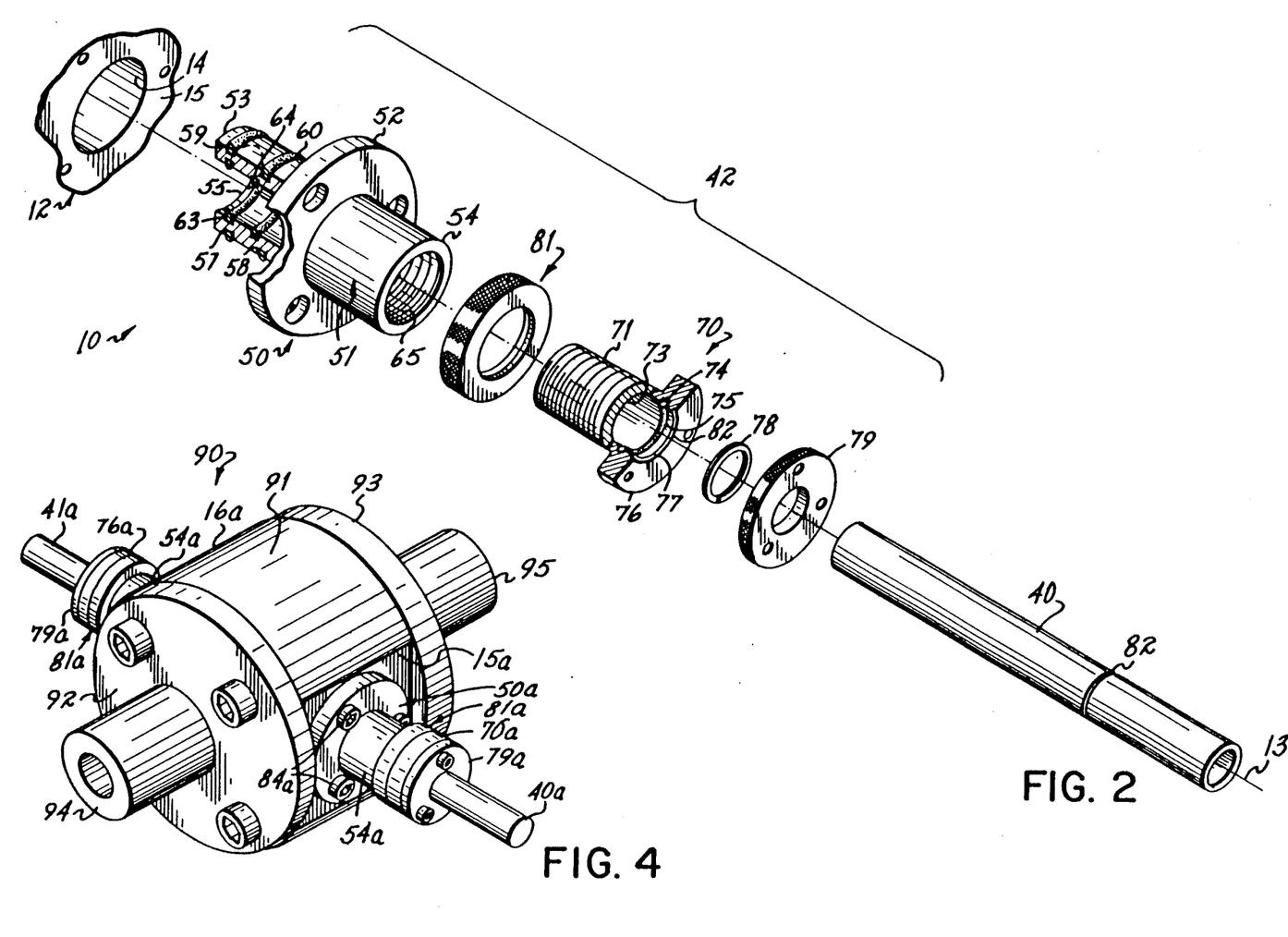
FIG. 2 is an enlarged detail in perspective form and partial cross-section of the probe and probe mounting elements of FIG. 1.
FIG. 4 is a perspective view of another embodiment of this invention used in a process line.
Figure 3:
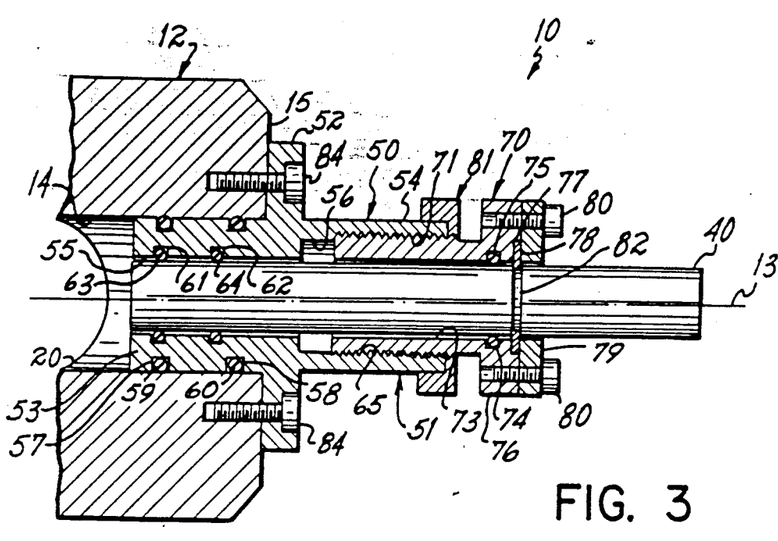
FIG. 3 is a cross-sectional view of the sample cell and probe mounting components of FIG. 1 shown in assembled interface form, the other components omitted for clarity.

Turning now to FIGS. 1, 2 and 3, there is illustrated therein a preferred embodiment of the invention in various forms. FIG. 1 discloses an in-line fiber optic probe interface 10 for use in a sample or recirculating line 11 having appropriate valving.

The interface 10 includes a sample cell or pipe cross 12 defining a predetermined optical axis 13 therein. The sample cell 12 includes a bore 14 extending from one side or face 15 to an opposed parallel side or face 16 therein. The bore 14 itself defines and is generated about optical axis 13.

Extending transversely through the sample cell 12 and intersecting perpendicularly with the bore 14 is a bore or fluid passage 20. This fluid passage 20 is connected with components of the sample line 11, and includes opposed fittings or adaptors 21,22 which are received within the sample cell 12. Valves 23 and 24 are mounted on the respective adaptors 21,22 and are connected to the respective pipes 25 and 26. Pipes 25 and 26 are connected with flange members 27,28, for example, which are components of a sample line 11. When the valves 23,24 are opened, the fluid in the sample line 11 is free to run through the components 21–28 and through the sample cell 12 between the ends of fiber optic probes, as will be described, for analysis. It will further be appreciated that the bore 20 is located on the axis 29 which in this particular embodiment is located perpendicularly to the axis 13.

It will also be appreciated in this embodiment that other adaptors 32,33 and valves 34,35 are provided on an axis 31 for sample cell flushing or access. Fluid can be run through the valves 34,35 and the adaptors 32,33 for cleaning out the sample cell 12 for cleaning the ends of the fiber optic probes, etc. Alternatively, the adaptors 32,33 can be removed from the sample cell 12 to provide access to the probe ends for cleaning, calibration, inspection or the like.

As noted above, the interface 10 includes means for mounting two probes 40,41 within the sample cell 12 on a common predetermined optical axis 13. Each of the probes 40,41 has respective means 42,43 for adjustably mounting the probe within the sample cell 12 such that each probe 40,41 is respectively centered on the optical axis 13 and such that each probe 40,41 can be longitudinally adjusted along the axis 13 without disturbing its optical alignment.

It should be appreciated that FIG. 2 discloses the particular probe mounting means 42 in enlarged form, and that the mounting means 43 is a duplicate of the means 42 in this embodiment. Also, it will be appreciated that FIG. 3 diagrammatically illustrates a cross sectional view of the mounting means 42 with the probe 40, all in assembled form.

Accordingly, and turning to FIGS. 2 and 3, it will be appreciated that the mounting means 42 includes a controller housing 50. The controller housing 50 includes a cylindrical body 51 and a radially extending flange 52 disposed centrally on the cylindrical body. The cylindrical body 51 has a forward end 53 and a rearward end 54. The cylindrical body also includes a first internal bore 55 and a more rearward internal bore 56, each having an axis in common with the predetermined optical axis 13 within the sample cell 12 as will be described. The outer diameter or surface of the end 53 of the cylindrical body 51 includes two spaced apart grooves 57 and 58 each containing a respective O-ring seal 59,60. The internal surface of the bore 55 is also provided with two grooves 61,62, each of which captures therein a respective O-ring seal 63,64. The inner diameter of the internal bore 56 is threaded, as at 65.

An optical pathlength controller 70, of generally cylindrical shape as shown is provided with threads 71 for cooperation with internal threads 65 on the controller housing. The pathlength controller 70 is threaded into that housing so that rotation of the controller moves the controller to the right or to the left as viewed in FIG. 3 depending on the direction of rotation. The controller has an internal bore 73 provided with a groove 74 with an O-ring 75 disposed therein.

The pathlength controller 70 further includes a radial flange 76 having a relieved portion 77 on the rearward face thereof for receiving a retainer ring 78 therein. The retainer ring 78 is captured in the groove 77 by means of a controller cap 79, attached to the controller by means of screw 80 or any other suitable means.

A lock ring 81 is provided with internal threads for mounting on the threads 71 of the path length controller 70 for locking the controller to the housing when the lock ring 81 is screwed down onto the rearward end 54 of the controller housing.

A fiber optic probe 40 is disposed within the controller housing 50 and pathlength controller 70. The probe 40 is provided with a groove 82 for receiving the retainer ring 78. It will be appreciated that the groove 82 or the relieved portion 77 is of sufficient dimension to capture the ring 78 while at the same time permitting that ring to rotate either with respect to the pathlength controller 70, the probe 40, or both. Accordingly, it will be appreciated that as the pathlength controller 70 is rotated counterclockwise, for example, as viewed in FIG. 4, the controller will move to the right, as seen in FIG. 3, with respect to the controller housing 50. This movement will carry with it the retainer ring 78 which, by virtue of its connection to the probe 40 in the groove 82, will also move the probe to the right or rearwardly with respect to the sample 12, thereby to adjust the gap between the forward end of the probe and the facing probe. At the same time, it will be appreciated that the probe 40 continues to be centered on the optical axis 13 by means of the forward O-rings 63,64 in the controller housing 50, and the O-ring 75 disposed in the pathlength controller 70. These O-rings tend to center the probe on the predetermined optical axis 13 and to maintain it on that optical axis even though the probe can be shifted lengthwise to the right or left as viewed in FIG. 3 by means of rotation of the pathlength controller.

When the components as described above are assembled, it will be appreciated that the controller housing 50 is first inserted into the sample cell 12, and particularly into the bore 14 therein. The seals 57,58 tend to center the controller housing 50 within the bore and on the predetermined optical axis 13. Thereafter, and in one preferred manner of securing the controller housing 50 to the sample cell 12, the holes as shown in FIGS. 3 and 4 are bored into the flange 52 and the bolts 84 are used to secure the controller housing to the sample cell 12. This method is particularly effective for centering the controller housing 50 in the sample cell 12 with particular regard to the optical axis 13. In other words, in the preparation of the sample cell 12, the face 15 is milled or machined on the sample cell 12 and the bore 14 is bored or drilled along the predetermined axis 13 with reference to the flat face 15. Thereafter, when the controller housing 50 is inserted into the bore 14, the O-ring seals 57 and 58 naturally tend to center the controller housing within the bore thus maintaining the axis of the controller housing coaxially with the predetermined optical axis 13. Once this centering has taken place, the holes are then drilled into the flanges so that the screws 84 do not tend to bind or otherwise draw the controller housing off-center. Thus, the controller housing 50 is indexed to the sample cell 12 by means of the bore 14.

It will also be appreciated that the threads 65 and 71 are cut into the controller housing 50 and the pathlength controller 70 in a very precise manner so that the controller housing axis in maintained coaxial with the axis of the controller housing 50 and the predetermined desired optical axis 13. Accordingly, the O-ring seal 75 serves to center the probe 40 within the pathlength controller 70. From FIG. 3, it will be appreciated that the probe is thus supported in multiple places along its length and along a predetermined axis 13 by means of the internal seals 63,64 and 75. Accordingly, the probe is supported by the self-centering seals as noted and is maintained on the optical axis 13. As a result, a shift in the materials making up the controller housing or the pathlength controller will not result in a significant shift in the axis of the probe 40 and that axis will thereby be maintained coaxially with the predetermined optical axis 13.

As noted above, the probe 40 can be of any suitable fiber optic probe type, such as for example, the fiber optic probe shown in U.S. Pat. Nos. 4,573,761 and 4,707,134 or in the commonly assigned and copending Pat. application, Ser. No. 07/236,571, filed Aug. 25, 1988 and entitled "Sealed Fiber Optic Probe". Fiber optic members may extend from the rearward or right-hand end of the probe 40 to a particular light source or to a receiving or analyzing means as is well known.

It will further be appreciated that in the manufacture of the sample cell, the face 16 is machined in the sample cell block in a plane parallel to the plane in which the face 15 resides. Accordingly, when the controller housing of the probe mounting means 43 is secured to the other side of the sample cell, the various pathlength controller and the various associated O-rings serve to center and align the controller housing, the pathlength controller and the probe 41 also along the common optical axis 13 in the same manner as has been described above. Accordingly, it will be appreciated that all of the mounting elements, including the controller housing and the pathlength controllers of the various probe mounting means are all referenced to the predetermined optical axis 13 for precise mounting of the respective probes thereon.

Of course, any probe can be mounted on any predetermined optical axis using similar components, whether the optical axes leading into the sample cell are predisposed on a common or on an intersecting basis, for example.

Returning again momentarily to FIG. 1, it will be appreciated that the ends of the probes 40,41 are spaced apart, with a gap therebetween, on common optical axis 13 within the sample cell 12. When a sample of fluid is admitted to the sample cell by means of the open valve 23,24 in the sample or recirculating line, light can be introduced through one probe and received by another across the fluid flowing in the gap and through the cell 12, whereby the fluid can be analyzed.

It will thus be appreciated that a gap is defined between the forward or facing ends of the probes 40,41 and that the gap length or the path from one probe face to the other can be controlled or adjusted by means of the pathlength controllers 70 as described above.

In another embodiment such as that shown in FIG. 4, an in-line fiber optic probe interface 90 is shown in an application constituting a spacer between the ends of two pipe flanges. In this embodiment, a sample cell 91 is configured to conform to the circumferential portions of pipe end flanges 92,93 mounted on the respective fluid pipes 94,95. Such an arrangement might be used, for example, where it is desirable to monitor fluid within a process or system. In this embodiment, the sample cell is inserted as a spacer between two flanged pipe ends as shown while probes 40a,41a are utilized to optically sample the fluid flowing through the pipes 94,95. In this embodiment, as shown in FIG. 4, similar elements to those described in the preferred embodiment above will be labelled with similar numbers accompanied by the suffix "a". In this embodiment, the probes 40a,41a are mounted in the sample cell 91 in the same manner as are the probes as shown in FIGS. 1 through 3. The sample cell is provided with opposed faces 15a, 16a on which are mounted respective controller housings such as controller housing 50a, such mounting elements and components maintaining the same advantages as discussed above. Accordingly, it will be appreciated that the alternative embodiment illustrates another application in which the probes and the mounting apparatus described herein can be utilized to advantage. There are many other applications in which the invention will find particular usefulness.

Accordingly, controlled optical alignment of fiber optic probes can be maintained under process conditions where pressure or temperatures changes, for example, might otherwise cause misalignment of the probes. While the pathlength of the gap across the probe ends is adjustable by means of the described pathlength controllers, it will also be appreciated that the probes themselves are not rotated during adjustment which might otherwise lead to misalignment. While a longitudinal groove could be cut in the probe or in the controller housing and associated with a solid key on the opposed element to maintain the probe from rotating, this is not necessary in the preferred embodiment as described.

Because the sample cells described are relatively small and symmetric they can be precisely machined using standard machining or lathe techniques and made interchangeable with many various cross type or processed designs.

In view of the elements as described above, the pathlength controller can be used to calibrate the gap distance between the probe ends by simply turning the probes in until they touch one another and then backing off or reversing and counting the turns while doing so to obtain a reasonably accurate estimate of the gap between the probes. Of course, the removable adaptors 32,33 provide access to the internal area of the sample cell 12 so that the gap can be appropriately calibrated.

Accordingly, the invention provides an in-line fiber optic probe interface wherein the only critical cut is the initial optical axis bore. The fine threads, O-ring grooves and retainer groove are precision turned on parts of reasonable size using standard lathe operations. The three point O-ring probe seal forces the probe onto the optical axis and minimizes off the axis wander while the removable wash out adaptors 32,33 allow on-line optimization and recalibration and enhance long term maintenance of the system.

These and other objectives and advantages will become readily apparent to those of ordinary skill in the art without departing from the scope of the invention and applicants intend to be bound only by the claims appended hereto.

We claim:
1. An in-line fiber optic probe interface comprising:
sample cell means having an optical axis therein;
fiber optic probe means disposed of said optical axis in said sample cell means,
a plurality of seal means circumferentially engaging said probe means at more than one location along the length thereof for sealing said probe means within said sample cell means and for maintaining said probe means in substantially consistent optical alignment on said predetermining optical axis defined in said sample cell means;
a bore in said sample cell means having an axis coaxial with and defining said optical axis,
a controller housing means disposed in said bore,
said controller housing means being sealed to said bore by first seal means,
a bore through said controller housing;
said probe means disposed in said controller housing bore, and
second seal means disposed between said probe means and said controller housing means.

2. An in-line fiber optic probe interface as in claim 1 further including:
a pathlength controller threaded into said control housing,
a bore in said pathlength controller,
said probe means disposed in said pathlength controller bore,
third seal means disposed between said probe means and said pathlength controller for sealing and probe means to said pathlength controller;
and wherein said first, second and third seal means comprise O-ring seals.

3. An in-line fiber optic probe interface as in claim 2 including a retainer ring operably connected between said controller and said probe for moving said probe when said controller is adjusted.

4. An in-line fiber optic probe interface as in claim 1 wherein said sample cell means comprises a pipe flange spacer.

5. An in-line fiber optic probe interface as in claim 1 wherein said optical axis is defined by a bore in said sample cell and further including a fluid passage extending through said sample cell means perpendicularly to an intersecting said bore.

6. An in-line fiber optic probe interface comprising:
a sample cell having a predetermined optical axis defined by a bore therein,
a controller housing aligned with said bore,
a pathlength controller mounted on said housing, and
a fiber optic probe sealed respectively to said housing and controller at multiple points along said probe for alignment of said probe on said optical axis.

7. An in-line fiber optic probe interface as in claim 6 including first O-ring seal means between said housing and said sample cell for aligning said housing in said bore on said axis.

8. An in-line fiber optic probe interface as in claim 7 including second O-ring seal means disposed between said probe and said controller housing and third O-ring seal means disposed between said probe and said controller for aligning said probe on said axis.

9. An in-line fiber optic probe interface as in claim 6 wherein said sample cell comprises a pipe flange spacer.

10. An in-line fiber optic probe interface as in claim 6 including a first fluid passage in said sample cell intersecting said bore and a second fluid passage in said sample cell intersecting said bore and said first fluid passage.

11. Apparatus for mounting a fiber optic probe on a predetermined optical axis defined by a bore in a sample cell and comprising:
a pathlength controller,
a controller housing disposed on said axis in said sample cell,
a fiber optic probe extending through said pathlength controller and said controller housing,
said pathlength controller threaded to said controller housing and connected to said probe for longitudinal adjustment of said probe along said optical axis with respect to said sample cell;
external O-ring seal means on said controller housing engaging said sample cell and coaxially aligning said controller housing with said optical axis,
internal O-ring seal means in said controller housing engaging said probe and centering said probe coaxially with said controller housing, and said optical axis, and
O-ring seal means between said probe and said pathlength controller for centering said probe on said optical axis.

12. An in-line fiber optic probe interface comprising:
a sample cell having two sides,
a bore extending through the sample cell on a predetermined optical axis, from one side to the other and having an end at each side,
a controller housing disposed in said bore at each end thereof,
a fiber optical probe disposed in each controller housing,
a pathlength controller operationally mounted on each controller housing and connected to the probe thereon for longitudinal probe adjustment along said optical axis,
O-ring seal means disposed between and sealing each of the respective probes to the respective controller housings; and
O-ring seal means disposed between and sealing each of the respective probes to the respective pathlength controllers.

13. An in-line fiber optic probe interface as in claim 12 wherein each said controller housing includes a cylindrical housing having an outside diameter less than that of said bore, a radial flange for engagement with a sample cell side and said O-ring seals between said controller housing to said sample cell aligning said housing with said optical axis.

14. An in-line fiber optic probe interface as in claim 12 further including:
a groove in said probe;
retainer ring disposed in said groove; and
means in said pathlength controller receiving said ring, said ring being captured for longitudinal travel with said controller to move said probe along said optical axis when said pathlength controller is moved along said axis.

15. An in-line fiber optic probe interface as in claim 14 wherein said path length controller is threaded to said controller housing.

16. An in-line fiber optic probe interface as in claim 12 wherein said sample cell comprises a pipe flange spacer.

17. An in-line fiber optic probe interface as in claim 12 including at least two O-ring seals between each of said probes and the respective controller housing.

18. An in-line fiber optic probe interface as in claim 12 including a first fluid passageway extending through said sample cell and intersecting said bore.

19. An in-line fiber optic probe interface as in claim 18 including a second passageway extending into said sample cell and intersecting said bore and said first passageway proximate ends of said probe.

20. A method of manufactured an in-line fiber optic probe interface including the steps of:
machining a flat face on a sample cell;
creating a bore in said sample cell from said flat face, said bore defining an optical axis in said cell;
inserting a controller housing having O-ring seal means thereon in said bore, said seals centering an axis of said controller housing on said optical axis defined by said bore;
inserting a fiber optic probe in said controller,
sealing and aligning said probe in said controller housing on said optical axis by means of second O-ring seal means disposed between said housing and probe; and
securing said probe to a pathlength controller adjustably mounted in said controller housing and sealing said probe to said pathlength controller on said optical axis by means of third O-ring seal means disposed between said probe and said controller.

21. Apparatus for mounting a fiber optic probe on a predetermined optical axis defined by a bore in a sample cell and comprising:
a pathlength controller,
a controller housing disposed on said axis in said sample cell, a fiber optic probe extending through pathlength controller and said controller housing, said pathlength controller threaded to said controller housing and connected to said probe for longitudinal adjustment of said probe along said optical axis with respect to said sample cell;

external seal means on said controller housing engaging said sample cell and coaxially aligning said controller housing with said optical axis, internal seal means in said controller housing engaging said probe and centering said probe coaxially with said controller housing, and said optical axis, and seal means between said probe and said pathlength controller for centering said probe on said optical axis.

22. An in-line fiber optic probe interface comprising:
a sample cell having two sides,
a bore extending through the sample cell on a predetermined optical axis, from one side to the other and having an end at each side,
a controller housing disposed in said bore at each end thereof,
a fiber optical probe disposed in each controller housing,
a pathlength controller operationally mounted on each controller housing and connected to the probe thereon for longitudinal probe adjustment along said optical axis,
seal means disposed between and sealing each of the respective probes to the respective controller housings; and
seal means disposed between and sealing each of the respective probes to the respective pathlength controllers.

23. A method of manufacturing an in-line fiber optic probe interface including the steps of:
machining a flat face on a sample cell;
creating a bore in said sample cell from said flat face, and bore defining an optical axis in said cell;
inserting a controller housing having first seal means thereon in said bore, said first seal means centering an axis of said controller housing on said optical axis defined by said bore;
inserting a fiber optic probe in said controller,
sealing and aligning said probe in said controller housing on said optical axis by means of second seal means disposed between said housing and probe; and
securing said probe to a pathlength controller adjustably mounted in said controller housing and sealing said probe to said pathlength controller on said optical axis by means of third seal means disposed between said probe and said controller.

24. An in-line fiber optic probe interface comprising:
sample cell means having an optical axis therein defined by a bore;
a controller housing sealed to said bore;
a pathlength controller mounted in said controller housing;

fiber optic probe means disposed on said optical axis in said sample cell means within said controller housing and controller; and a plurality of seal means circumferentially engaging said probe means at more than one location along the length thereof and between both said probe and said controller housing and said probe and said pathlength controller for sealing said probe means within said sample cell means and for maintaining said probe means in substantially consistent optical alignment on said predetermined optical defined in said sample cell means.

25. An in-line fiber optic probe interface comprising:
sample cell means having an optical axis therein;
a bore in said sample cell means having an axis coaxial with and defining said optical axis.
a controller housing means disposed in said bore,
said controller housing means being sealed to said bore by O-ring seals, and aligned thereby with said optical axis;
a bore through said controller housing,
probe means disposed in said controller housing bore and on said optical axis,
O-ring seal means disposed between said probe means and said controller housing means, aligning said probe on said optical axis,
a pathlength controller threaded into said control housing,
a bore in said pathlength controller aligned with said optical axis,
said probes means disposed in said pathlength controller bore
O-ring seal means disposed between said probe means and said pathlength controller for sealing said probe means to said pathlength controller and aligning said probe means with said optical axis;
a groove in said probe means; and
a retainer ring operably connected between said controller and said probe means groove for moving said probe means along said optical axis when said controller is adjusted therealong.

26. An in-line fiber optic probe interface comprising:
sample cell means;
a bore in said sample cell means having an axis coaxial with and defining an optical axis,
a controller housing means disposed in said bore,
said controller housing means being sealed to said bore by first O-ring seal means,
a bore through said controller housing,
a probe means disposed in said controller housing bore on said optical axis, and
second O-ring seal means disposed between said probe means and said controller housing means,
said second O-ring seal means circumferentially engaging said probe means at more than one location along the length thereof for sealing said probe means within said sample cell means and for maintaining said probe means in substantially consistent optical alignment on said predetermined optical axis defined in said sample cell means.

* * * * *

UNITED STATES PATENT AND TRADEMARK OFFICE
CERTIFICATE OF CORRECTION

PATENT NO. : 4,988,155

DATED : January 29, 1991

INVENTOR(S) : Richard S. Harner et al.

It is certified that error appears in the above-identified patent and that said Letters Patent is hereby corrected as shown below:

Column 10, line 22 "retainer" should correctly read -- a retainer --.

Column 10, line 44 "manufactured" should correctly read -- manufacturing --

Column 10, line 48 "said" should correctly read -- and --.

Column 10, line 49 "O-ring" should correctly read -- first --.

Signed and Sealed this

Fifteenth Day of September, 1992

*Attest:*

DOUGLAS B. COMER

*Attesting Officer*   *Acting Commissioner of Patents and Trademarks*